US00PP09121P

United States Patent [19]

Tachibana et al.

[11] Patent Number: Plant 9,121

[45] Date of Patent: Apr. 25, 1995

[54] VERBENA PLANT 'SUNMAREF TP-L'

[75] Inventors: Ryuichi Tachibana, Yamato; Yuji Tamura, Kofu; Ushio Sakazaki, Hikone, all of Japan

[73] Assignee: Suntory Limited, Osaka, Japan

[21] Appl. No.: 225,078

[22] Filed: Apr. 8, 1994

Related U.S. Application Data

[63] Continuation of Ser. No. 100,156, Aug. 2, 1993.

[51] Int. Cl.[6] ..... A01H 5/00

[52] U.S. Cl. ..... Plt./87

[58] Field of Search ..... Plt. 87

*Primary Examiner*—James R. Feyrer

*Attorney, Agent, or Firm*—Burns, Doane, Swecker & Mathis

[57] ABSTRACT

Disclosed herein is a decumbent type verbena plant having long stems. The plant has abundant branching wherein each node of the branches the contacts the ground commonly forming deep-spreading roots. The plant forms numerous flowers that appear as ascending spikes in a great profusion of blooms. The flowers exhibit petals having a strong purple color, with a small very pale purple eye. The plant is highly resistant to heat, cold, diseases, and pests.

4 Drawing Sheets

This application is a continuation of application Ser. No. 08/100,156, filed Aug. 2, 1993, now abandoned.

BACKGROUND OF THE VARIETY

The present invention relates to a new and distinct variety of Verbena plant obtained from crossing one verbena plant (♀) which was selected from crossing 'Rainbowcarpet Brightpurple' (♀) and a wild type of verbena plant (♂) native to Brazil, and 'Verbena tenera' (♂). The 'Rainbowcarpet Brightpurple' parent is botanically known as *Verbena×hybrida* Voss.

Verbena of the presently commercialized 'Rainbowcarpet' series is semi-erect growth habit having medium stems, medium branching, and a scant number of flowers, and has moderate tolerance to heat and cold. Accordingly, this invention was aimed at obtaining a new variety having a spreading growth habit, a high level of branching, numerous flowers, high tolerance to heat and cold, and resistance to diseases and pests, which is superior to those of the 'Reinbowcarpet' series, and having a purple flower color.

A crossing of 'Rainbowcarpet Brightpurple' as the female parent and a wild type of verbena plant native to Brazil as the pollen parent was practiced, in 1988, at the Plant Biotechnology Laboratory, Institute for Fundamental Research of Suntory Ltd., residing at 2913-1 Torihara, Hakushu-cho, Kitakoma-gun, Yamanashi-ken, Japan. From this crossing, 75 seedlings were obtained in the spring of 1988, and then a crossing of 10 seedlings of the 75 seedlings as the female parent and 'Verbena tenera' the from Takii Seed & Seedling Corp., as the pollen parent was practiced at the same place. From this crossing 25 seedlings were obtained in the summer of 1988, from which 4 seedlings were selected, propagated by cuttings, and then grown as a trial by flower bedding and potting from the spring of 1989. Only one of the 4 resulting plants was selected. The botanical characteristics of the finally-selected plant were then examined, using similar varieties, 'Rainbowcarpet Brightpurple', and 'Rainbowcarpet Rose' for comparison, from the spring of 1990. As a result, it was concluded that this verbena plant is distinguishable from any other variety whose existence is known to us, and this new variety of verbena plant was named 'Sunmaref TP-L' (Tapien Lilca ®.)

In the following description, the color-coding is in accordance with the Horticultural Color Chart of The Royal Horticultural Society, London, England (R.H.S. Color Chart), and the Inter-Society Color Council-Nation Bureau of Standards Color Name) (ISCC-NBS Color Name). A color chart based on The Japan Color Standard for Horticultural Plants (J.H.S. Color Chart) is also added for reference.

'Rainbowcarpet Brightpurple' used as the female parent in obtaining the female parent in the breeding of this new variety 'Sunmaref TP-L' is one of the 'Rainbowcarpet' series bred by the Takii Seed & Seedling Corp., Japan. The 'Rainbowcarpet' series includes 'Rainbowcarpet Rose', 'Rainbowcarpet White', and the like. The main botanical characteristics of 'Rainbowcarpet Brightpurple' are as follows.

Plant:

*Growth habit.*—Semi-erect.

*Plant height.*—25–30 cm.

*Spreading area of plant.*—30–35 cm.

*Blooming period.*—Late April to November.

Stem:

*Diameter.*—2–3 mm.

*Anthocyanin pigmentation.*—Absent.

*Branching.*—Medium.

*Pubescence.*—Scant.

*Length of internode.*—35–40 mm.

Leaf:

*Phyllotaxis.*—Opposite.

*Shape of blade.*—Broadly ovate.

*Length.*—20–25 mm.

*Width.*—15–20 mm.

*Depth of incision.*—Deep.

*Color.*—Deep yellow green (R.H.S.141A, J.H.S. 3706).

*Pubescence.*—Scant.

Flower:

*Direction.*—Ascending.

*Outward curvature of petal.*—Slightly curved.

*Diameter.*—10–15 mm.

*Length.*—13–15 mm.

*Color.*—Vivid purple (R.H.S. 82A, J.H.S. 8606).
*Color intensity.*—Absent.
*Overlapping of petals.*—Separate.
*Spike.*—25–30 mm in length; and 30–35 mm in diameter.
*Calyx.*—0.5–1.0 cm.
*Anthocyanin pigmentation of calyx limb.*—Present.
*Peduncle.*—Less than 2 mm in diameter; and 6.0–8.0 cm in length.
*Number of flowers.*—Few (9±2).
*Productive organs.*—1 pistil and 5 stamens.
*Physiological and ecological characteristics.*—Moderate resistances to pests and diseases, and moderate tolerance to cold and heat.

The plant used as the pollen parent in the obtaining of the female parent in the breeding of this new variety 'Sunmaref TP-L' is a wild type of verbena plant native to South Brazil and this wild type of plant is presently maintained at the Plant Biotechnology Laboratory of Suntory Ltd. The main botanical characeristics of the said pollen parent are as follows.

Plant:
*Growth habit.*—Spreading.
*Plant height.*—10–15 cm.
*Plant extension.*—80–100 cm.
*Blooming period.*—Late April to November.
Stem:
*Extending.*—40–50 cm.
*Diameter.*—2–3 mm.
*Anthocyanin pigmentation.*—Absent.
*Branching.*—Abundant.
*Pubescence.*—Medium.
*Length of internode.*—20–30 mm.
Leaf:
*Phyllotaxis.*—Opposite.
*Shape of blade.*—Ovate.
*Length.*—15–20 mm.
*Width.*—10–15 mm.
*Depth of incision.*—Deep.
*Color.*—*Deep yellow green (R.H.S.* 141A, J.H.S. 3706).
*Pubescence.*—Medium.
Flower:
*Direction.*—Ascending.
*Outward curvature of petal.*—Slightly curved.
*Diameter.*—10–15 mm.
*Length.*—12–15 mm.
*Color.*—Brilliant purple (R.H.S. 86C, J.H.S. 8604).
*Color intensity.*—Absent.
*Overlapping of petals.*—Separate.
*Spike.*—30–40 mm in length; and 35–40 mm in diameter.
*Calyx.*—0.5–1.0 cm in length.
*Anthocyanin pigmentation of calyx limb.*—Absent.
*Peduncle.*—1–2 mm in thickness, and 30–50 mm in length.
*Number of flowers.*—Medium (10±2).
*Productive organs.*—1 pistil and 5 stamens.
*Physiological and ecological characteristics.*—High resistance to diseases and pests, and high tolerance to heat and cold.

The pollen parent used in the in the breeding of 'Sunmaref TP-L' is 'Verbena tenera' obtained from the Sakata Seed Corp., Japan. The main botanical characteristics of the 'Verbena tenera' are as follows.

Plant:
*Growth habit.*—Semi-erect.
*Plant height.*—20–25 cm.
*Plant extension.*—40–50 cm.
*Blooming period.*—Late April to November.
Stem:
*Diameter.*—Less than 2 mm.
*Anthocyanin pigmentation.*—Absent.
*Branching.*—Medium to abundant.
*Pubescence.*—Medium.
*Length of internode.*—35–45 mm.
Leaf:
*Phyllotaxis.*—Opposite.
*Shape of blade.*—Cut deeply into the branches progressively in 2 to 3, or more stages.
*Length.*—20–25 mm.
*Width.*—20–25 mm.
*Depth of incision.*—Deep.
*Color.*—Deep yellow green (R.H.S. 141A-B, J.H.S. 3706).
*Pubescence.*—Medium.
Flower:
*Direction.*—Ascending.
*Outward curvature of petal.*—Slightly curved.
*Diameter.*—15–20 mm.
*Length.*—10–15 mm.
*Color.*—Strong purple (R.H.S. 81B-82B, J.H.S. 8604).
*Color intensity.*—Absent.
*Overlapping of petals.*—Separate.
*Spike.*—30–40 mm in length; and 35–40 mm in diameter.
*Calyx.*—0.5–1.0 cm in length.
*Anthocyanin pigmentation of calyx limb.*—Absent.
*Peduncle.*—2 mm in thickness, and 8.0–10.0 cm in length.
*Number of flowers.*—Medium (10±2).
*Productive organs.*—1 pistil and 5 stamens.
*Physiological and ecological characteristics.*—Moderate resistance to diseases and pests, and moderate tolerance to cold and heat.

The new variety of verbena plant, 'Sunmaref TP-L' was asexually reproduced by cuttings at the aforementioned the Plant Biotechnology Laboratory, Institute for Fundamental Research of Suntory Ltd., and the homogeneity and stability thereof was confirmed.

SUMMARY OF THE VARIETY

The new variety of verbena plant has a spreading growth habit with very long stems and is very low in height, and spreading area of plant is broad and thus is very different from similar varieties, 'Rainbowcarpet Brightpurple', and 'Rainbowcarpet Rose'. The plant has abundant branching and forms numerous flowers in ascending spikes, with a great profusion of blooms which are clearly distinguishable from the similar varieties, 'Rainbowcarpet Brightpurple', and 'Rainbowcarpet Rose', and the whole bush remains in bloom for a considerable period of time, longer than the blooming period of 'Rainbowcarpet Rose'. The length of internode of the new variety is slightly longer than that of similar varieties, and the each node that contacts the ground commonly forms deep-spreading roots that hold the plant firmly in the ground. The flowers have petals having a strong purple coloration, with a small very pale purple eye. The plant is highly resistant to cold, heat, diseases, and pests.

DESCRIPTION OF THE VARIETY

Figure 1:
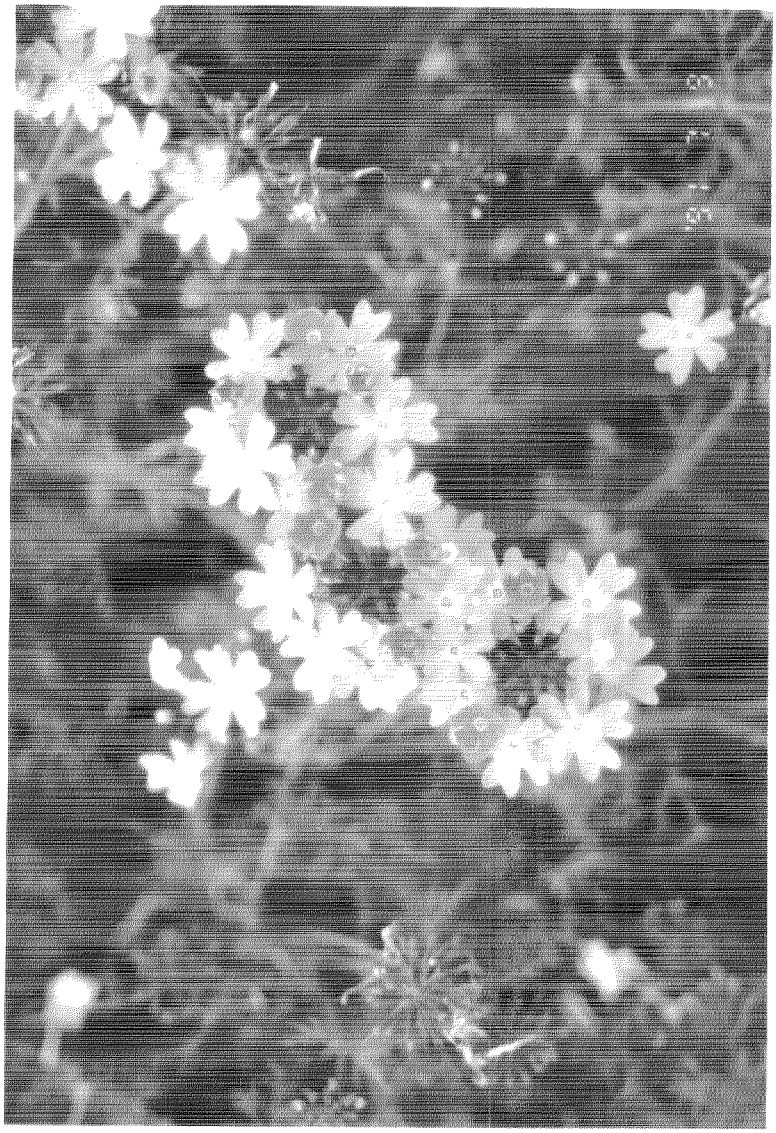
FIG. 1 is photograph of flowers of the new variety of verbena plant.
Figure 2:
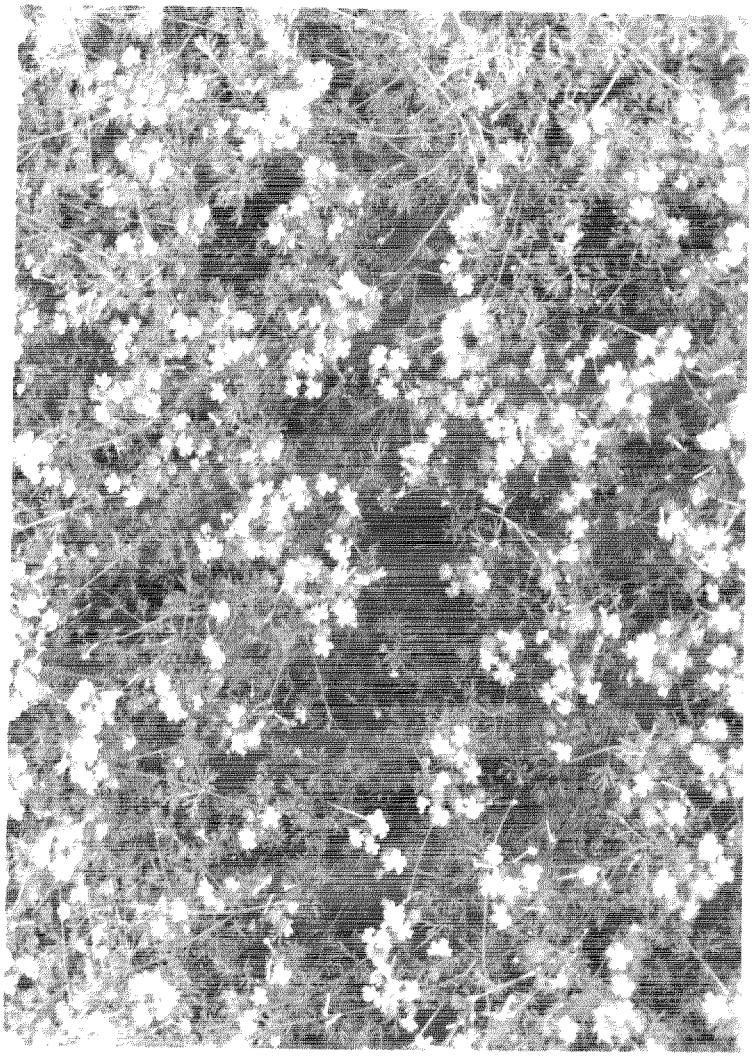
FIG. 2 is a photograph giving a partial view of the new variety of verbena plant planted in a flower bed.
Figure 3:
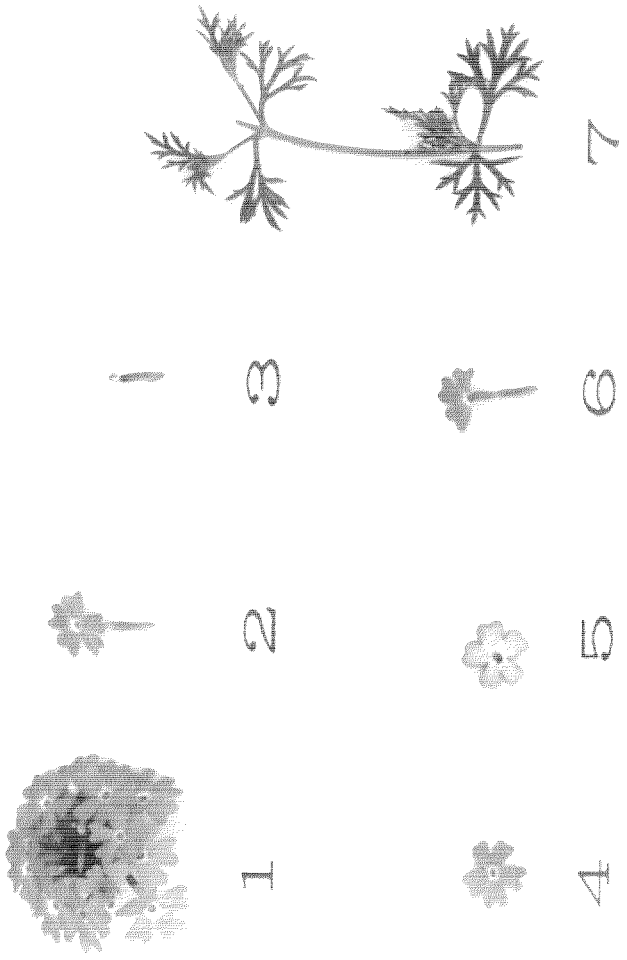
FIG. 3 is a photograph showing, in numerical order, a cluster (1), a flower (2), a bud (3), a surface view of the flower (4), a rear view of the flower (5), a cross-sectional view of the flower (6), and a branch (7), of the new variety of verbena plant.
Figure 4:
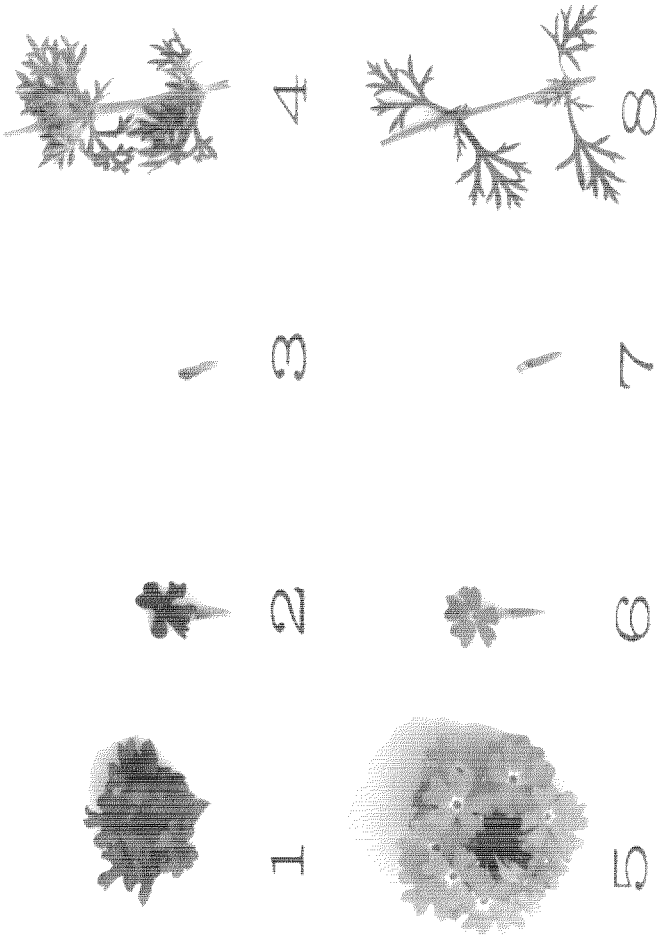
FIG. 4 is a photograph showing, in numerical order, a cluster (1), a flower (2), a bud (3), and a branch (4) of a similar variety 'Rainbowcarpet Brightpurple', in comparison with corresponding items (5–8) of the new variety of verbena plant.

The botanical characteristics of the new and distinct variety of verbena plant, 'Sunmaref TP-L' are as follows.

Plant:

*Growth habit.*—Spreading.

*Plant height.*—15–20 cm.

*Spreading area of plant.*—The stem extends to a length of 50–75 cm, and thus the spreading area of the plant is 100–150 cm.

*Growth.*—Very vigorous with abundant branching and a great profusion of blooms; the whole bush remaining in bloom for a considerable period of time.

*Blooming period.*—Late April to November, in all areas of Japan.

*Ploidy.*—Normal.

Stem:

*Diameter.*—2–3 mm.

*Anthocyanin pigmentation.*—Present.

*Branching.*—Abundant; each node in the branches contacting the ground takes deep spreading roots.

*Length of internode.*—35–50 mm.

*Pubescence.*—Some pubescence commonly is present.

Leaf:

*Phyllotaxis.*—Opposite.

*Shape of blade.*—Progressively cut deeply into the branches in 2 to 3, or more stages.

*Length.*—10–15 mm.

*Width.*—10–15 mm.

*Depth of incision.*—Deep.

*Color.*—Moderate yellow green (R.H.S. 137C, J.H.S. 3712). Some slight reddish coloration commonly appears during the winter.

*Pubescence.*—Some pubescence commonly is present.

*Stipules.*—Absent.

*Direction.*—Ascending.

*Outward curvature of petal.*—Slightly curved.

*Diameter.*—15–20 mm.

*Length.*—10–15 mm.

*Cluster.*—Umbel form from 15 flowers.

*Color.*—Petal has strong purple (R.H.S. 81B-82B, J.H.S. 8605) with an eye color which is very pale purple. (R.H.S. 85D-91D, J.H.S. 8302)

*Color intensity.*—Absent.

*Overlapping of petals.*—Separate.

*Spike.*—20–30 mm in length; and 40–45 mm in diameter.

*Calyx.*—0.5–1.0 cm. It is typical for the genes.

*Anthocyanin pigmentation of calyx limb.*—Generally present in no particular pattern.

*Peduncle.*—1–2 mm in thickness; and 8.0–10.0 cm in length.

*Number of flowers.*—Abundant (15±2).

*Reproductive organs.*—1 pistil and 5 stamens. Seeds commonly are formed in a very low frequency.

Physiological and ecological characteristics: High tolerance to heat and cold. The new variety is a perennial and has satisfactory withstood temperatures as low as 0° C. and as high as 35° C. when grown in the field at Osaka, Japan. Also strong resistances to pests and disease, particularly powdery mildew. The pinching of spent spikes commonly is necessary for a continuation of blossom production. Thinning is not required to maintain the new variety.

This new variety of verbena plant is most suitable for flower bedding and potting, and is further excellent for ground cover. The new variety grows well in full sun, and has no particular fertilizer requirement for good performance. The plant also grows well in the shade, but commonly does not bloom well in the absence of sunlight. A very strong resistance to mildew is exhibited by the new variety.

The plant of this new variety, 'Sunmaref TP-L' is presently planted and maintained at the Plant Biotechnology Laboratory, Institute for Fundamental Research of Suntory Ltd., residing at 2913-1 Torihara, Hakushu-cho, Kitatama-gun, Yamanashi-ken, Japan.

We claim:

1. A new and distinct variety of verbena plant, substantially as herein illustrated and described, characterized particularly as to novelty by (A) a spreading growth habit with long stems, (B) the formation of abundant branching with each node of said spreading branches that contacts the ground commonly forming deep-spreading roots, (C) the formation of many flowers borne on ascending spikes to create a great profusion of blooms, (D) the formation of flowers that exhibit petals having a strong purple coloration with a small very pale purple eye coloration, and (E) a high resistance to heat, cold, rain, diseases, and pests.

* * * * *